United States Patent [19]

Robertson et al.

[11] Patent Number: 4,696,901
[45] Date of Patent: Sep. 29, 1987

[54] IMMOBILIZATION OF MICROORGANISMS ON A PLASTIC CARRIER

[75] Inventors: Brian W. Robertson; Gareth T. Phillips, both of Sittingbourne, England

[73] Assignees: Shell Internationale Research Maatschappij B.V., The Hague; Gist Brocades N.V., Delft, both of Netherlands

[21] Appl. No.: 558,749

[22] Filed: Dec. 7, 1983

[30] Foreign Application Priority Data

Dec. 23, 1982 [GB] United Kingdom ............... 8236719

[51] Int. Cl.[4] .................... C12N 11/08; C12N 11/00; C12N 1/26
[52] U.S. Cl. .................................. 435/180; 435/174; 435/248
[58] Field of Search ............... 435/174, 177, 180, 248

[56] References Cited

U.S. PATENT DOCUMENTS

| | | | |
|---|---|---|---|
| 3,642,577 | 2/1972 | Gorring | 435/248 X |
| 3,888,736 | 6/1975 | Iizuka et al. | 435/248 |
| 4,011,135 | 3/1977 | Kamatani et al. | 435/180 X |
| 4,332,904 | 6/1982 | Kurane et al. | 435/262 |
| 4,504,547 | 3/1985 | Horodniceanu et al. | 435/180 X |
| 4,537,790 | 8/1985 | Horodniceanu et al. | 435/180 X |
| 4,547,463 | 10/1985 | Sakata et al. | 435/180 |

FOREIGN PATENT DOCUMENTS

| | | | |
|---|---|---|---|
| 884876 | 12/1980 | Belgium. | |
| 112597 | 7/1984 | European Pat. Off. | 435/180 |
| 1924333 | 1/1970 | Fed. Rep. of Germany | 424/93 |
| 56-8691 | 1/1981 | Japan | 435/180 |

OTHER PUBLICATIONS

American Chemical Society (ACS) Symp. Ser. 1979, vol. 106, pp. 73–86.

*Primary Examiner*—David M. Naff
*Assistant Examiner*—Shawn P. Foley

[57] ABSTRACT

Hydrocarbon utilizing microorganisms are immobilized on a plastic carrier in an aqueous nutrient medium to which a minor amount of a water-immiscible hydrocarbon substrate has been added. The water-immiscible hydrocarbon is preferably hexadecane or dodecylcyclohexane and the plastic carrier is preferably polytetrafluoroethylene. Presence of the water-immiscible hydrocarbon substrate results in increased loading of microorganisms on the carrier.

13 Claims, 2 Drawing Figures

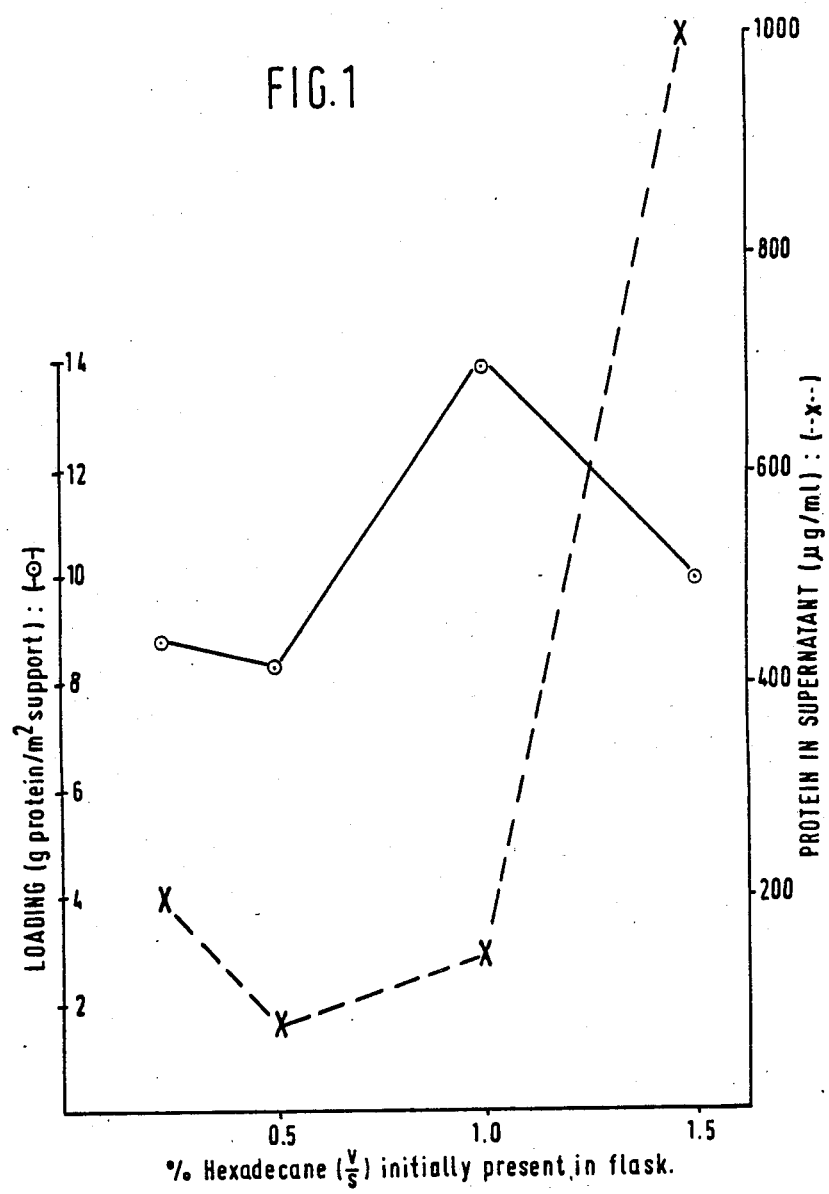

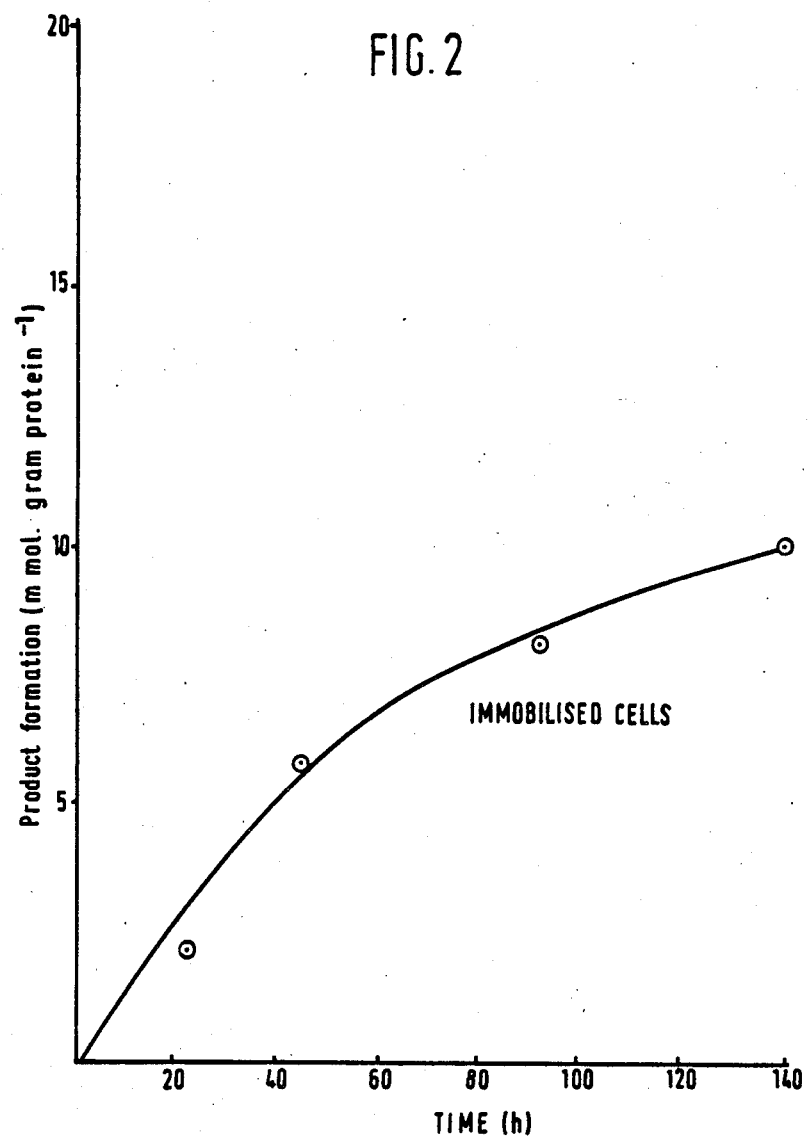

IMMOBILIZATION OF MICROORGANISMS ON A PLASTIC CARRIER

The present invention relates to a process for the immobilisation of microorganisms on a plastic carrier.

From American Chemical Society (ACS) Symp. Ser. 1979 V 106, pp 73–86 it is known to immobilise microorganisms such as Pseudomonas aeruginosa on a plastic carrier like polyvinyl chloride (PVC) and melt blown polypropylene (PP) webs. Pseudomonas aeruginosa is immobilised on small pieces (less than 1 cm$^2$) of PVC which have been loosely packed in a glass column. The void volume is filled with a sterile mineral salts solution.

A beef-broth culture of Pseudomonas aeruginosa ATCC 13388 is inoculated to the mineral salts solution. The microorganism grows on the PVC-plastic using the softeners in PVC as a carbon source.

In the article of the ACS Symp. Ser. it is postulated that the plastic may serve as sole carbon source required for the multiplication of bacteria but that an additional carbon source promotes the initial phase of attachment, due to the better adhesion of a large number of quickly multiplying bacteria, which become attached as a new layer to the layer of bacteria fixed on the plastic surface. Water-miscible substrates like glucose and methanol are mentioned as additional C-sources. In ACS Symp. Ser. 1979 V 106. pp 73–86 it is further described how Pseudomonas aeruginosa is immobilised on polypropylene (PP). Melt blown, fine PP filaments which are inert first undergo plasma treatment to enhance the efficiency of the PP web for bacterial attachment. Then the Pseudomonas aeruginosa cells are immobilised on the plastic surfaces by immersing the plastic into a growing Pseudomonas aeruginosa culture for 72 hours.

It has now been found that hydrocarbon-utilising microorganisms can be surprisingly better immobilised onto plastic carriers if the immobilisation is carried out in an aqueous nutrient medium to which a minor amount of a water-immiscible hydrocarbon substrate has been added. An important advantage of this process is that the plastic carriers need not undergo a plasma pretreatment of the plastic surface nor is it required that they contain plasticisers. Therefore the present invention provides a process for the immobilisation of one or more hydrocarbon utilising microorganisms on a plastic carrier in which the immobilisation is carried out in an aqueous nutrient medium to which a minor amount of water-immiscible hydrocarbon substrate has been added. The amount of water-immiscible hydrocarbon substrate to be added to the nutrient aqueous medium is preferably in the range of 0.1–3 ml per 100 cm$^2$ plastic carrier surface area.

The water-immiscible hydrocarbon substrate may suitably be a linear or cyclic hydrocarbon or a mixture thereof. Preferably the water-immiscible hydrocarbon substrate is selected from the group consisting of alkanes having 12–18 carbon atoms or mixtures thereof. Most preferred hydrocarbon substrates are hexadecane and dodecylcyclohexane. The aqueous nutrient medium, which should be sufficient to submerge the plastic carrier or plastic carriers, comprises suitably assimable sources of nitrogen and essential mineral salts.

The temperature at which the present process is carried out is preferably in the range of 25°–37° C. Suitable plastic carriers are synthetic polymers of which the group consisting of polytetrafluoroethylene, nylon, polyethylene and polyvinylchloride is preferred. Of these polymers polytetrafluoroethylene and polyethylene are most preferred. Microorganisms which utilise hydrocarbons as a nutrient material include yeasts, fungi, algae and bacteria. Microorganisms which are preferably applied in the present process are selected from the genera consisting of Mycobacterium, Corynebacterium Arthrobacter and Pseudomonas. Preferred species are Mycobacterium rhodochrous 7E1C NCIB 9703, Mycobacterium lacticolum NCIB 9739 and Pseudomonas aeruginosa 473 (as first described by Thijsse and van der Linden in Ant.v.Leeuwenhoek 24 (1958)).

The present invention further provides a plastic carrier on which microorganisms have been immobilised according to the present process. The microorganisms-containing plastic carrier may be used in methods of removal of heavy metals as described in ACS Symp. Ser. 1979 V·106, pp 73–86 and for the conversion of hydrocarbons to acids.

BRIEF DESCRIPTION OF THE DRAWINGS

FIG. 1 shows the effect of hexadecane concentration on the immobilization of Mycobacterium rhodochrous on polyethylene.

FIG. 2 shows the production of cyclohexylacetic acid using M. rhodocrous immobilized on polyethylene and dodecylcyclohexane as the substrate.

The present invention will be further described with reference to the following examples.

EXAMPLE I

Immobilisation of several microorganisms on polytetrafluoroethylene (PTFE) in the presence of either hexadecane, glucose or sodium acetate Autoclaved shake flasks (250 ml) containing the support (150 cm×0.3 cm PTFE ribbon), 100 ml Finnerty medium* (synthetic mineral salts medium), and either 0.25% v/v hexadecane, 0.2% v/v glucose or 0.5% v/v sodium acetate were inoculated with the desired organism. Some organisms required the presence of 0.01% yeast extract for growth. The organisms were grown at 30° C. on an orbital shaker at 220 rpm for 4 to 5 days. The quantity of cells on the support and in the supernatant were analysed by protein determination (as described in J. Biol. Chem. 193:262 (1951)) following solubilisation in 0.5N NaOH.

| Composition of Finnerty medium | g l$^{-1}$ |
|---|---|
| (NH$_4$)$_2$SO$_4$ | 5 |
| KH$_2$PO$_4$ | 4 |
| Na$_2$HPO$_4$ | 6 |
| MgSO$_4$7H$_2$O | 0.2 |
| CaCl$_2$ 2H$_2$O | 0.05 |
| FeSO$_4$ | 0.01 | pH of medium 7.0

The results are expressed as g protein/m$^2$ support (Table 1), and as the ratio of total protein on the support/total protein in the supernatant (Table II).

EXAMPLE II

Immobilisation of several microorganisms on polyethylene (PE) in the presence of either hexadecane, glucose or sodium acetate The immobilisation was carried out according to Example I except that the polyethylene ribbon was autoclaved loosely packed because of its tendency to meet and resolidify. The results are shown in Table I and Table II.

WHP 100/120, programmed for 60°–220° C. at 10° per min with nitrogen (30 ml/min) as carrier phase.

TABLE I

| | Loading (g protein/m² support) | | | | | |
|---|---|---|---|---|---|---|
| | PTFE | | | POLYETHYLENE | | |
| | Hexadecane | Glucose | Sodium Acetate | Hexadecane | Glucose | Sodium Acetate |
| M. rhodochrous 7E1C NCIB 9703 | 6.9 | 1.2 | 0.005 | 10.5 | 2.6 | 0.008 |
| C. hydrocarboxydans ATCC 21761 | 1.7 | 0.34 | 0.16 | 2.4 | 0.24 | 0.20 |
| Ps. aeruginosa 473 | 2.3 | 0.60 | 0.32 | 5.9 | 1.4 | 0.55 |
| A. paraffineus DSM 312 | 3.8 | — | — | 6.6 | — | — |
| M. lacticolum NCIB 9739 | 7.1 | — | — | 5.9 | — | — |

M = Mycobaterium
C = Corynebacterium
Ps = Pseudomonas
A = Arthrobacter

TABLE II

Ratio: $\frac{\text{Protein on support}}{\text{Protein in supernatant}}$

| | PTFE | | | POLYETHYLENE | | |
|---|---|---|---|---|---|---|
| | Haxadecane | Glucose | Sodium Acetate | Hexadecane | Glucose | Sodium Acetate |
| M. rhodochrous E1C NCIB 9703 | 6.4 | 0.24 | 0.006 | 33.0 | 0.30 | 0.005 |
| C. hydrocarboxydans ATCC 21761 | 1.4 | 0.05 | 0.03 | 0.88 | 0.02 | 0.02 |
| Ps. aeruginosa 473 | 0.35 | 0.10 | 0.05 | 0.63 | 0.08 | 0.04 |
| A. parrafineus DSM 312 | 1.6 | — | — | 1.2 | — | — |
| M. lacticolum NCIB 9739 | 17.7 | — | — | 5.8 | — | — |

The data in tables I and II clearly show the substantially better immobilisation which occurs when the immobilisation process is carried out in the presence of the water-immiscible hydrocarbon substrate hexadecane as compared with the water-miscible substrates glucose and sodium acetate.

EXAMPLE III

Effect of substrate concentration on the immobilisation of *Mycobacterium rhodochrous* on PE.

Shake flasks containing autoclaved polyethylene, Finnerty medium (100 ml) and hexadecane (0.25, 0.5, 1.0 or 1.5% v/v) were incubated on an orbital shaker (30° C., 220 rpm). Growth on the support (surface area of about 50 cm²) and in the supernatant was measured after five days. FIG. I gives the values at different volume percentages of hexadecane in the flask and for the amounts of protein which appear in the supernatant in μg/ml. A maximum loading (immobilisation) of microorganisms on 50 cm² PE occurs at a hexadecane percentage of 1.0% v/v which corresponds with 1 ml hexadecane.

EXAMPLE IV

Conversion of dodecylcyclohexane into cyclohexylacetic acid using *M. rhodochrous* immobilised on polyethylene M. Rhodochrous was grown on Finnerty medium in the presence of polyethylene (as in Example II) and 0.5% dodecylcyclohexane for four days. The immobilised cells (20.8 mg protein) were resuspended in nitrogen free medium (100 ml) containing 0.2% dodecylcyclohexane and incubated at 30° and 220 rpm. Samples (2.5 ml) were taken at time intervals, acidified with 5N sulphuric acid and extracted into diethylether. The extract was assayed for cyclohexylacetic acid using gas liquid chromatography on 2 mm × 50 cm, 3% OV-1 on The production of cyclohexylacetic acid is shown in FIG. 2.

We claim:

1. In a process for the immobilisation of one or more hydrocarbon-utilising microorganisms on a plastic carrier in which the immobilisation is carried out in an aqueous nutrient medium, the improvement comprising adding to the nutrient medium from about 0.1-3 ml of a water-immiscible hydrocarbon substrate per 100 cm² of plastic carrier surface area.

2. Process as claimed in claim 1 wherein said plastic carrier does not contain plasticizer and is not plasma treated.

3. Process as claimed in claim 1 or 2 in which the water-immiscible hydrocarbon substrate is selected from the group consisting of alkanes having 12–18 carbon atoms and mixtures thereof.

4. Process as claimed in claim 3 in which the water-immiscible hydrocarbon substrate is hexadecane.

5. Process as claimed in claim 3 in which the immobilisation is carried out at a temperature which is in the range of 25°–37° C.

6. Process as claimed in claim 3 in which the water-immiscible hydrocarbon substrate is dodecylcyclohexane.

7. Process as claimed in claim 5 in which the plastic carrier is selected from the group consisting of polytetrafluoroethylene, nylon, polyethylene and polyvinylchloride.

8. Process as claimed in claim 7 in which the plastic carrier is polytetrafluoroethylene.

9. Process as claimed in claim 7 in which the hydrocarbon utilizing microorganism is selected from the group consisting of *Mycobacterium rhodochrous* 7E1C NCIB 9703, *C. hydrocarboxydans* ATCC 21761 and *Pseudomonas aeruginosa* 473.

10. Process as claimed in claim 7 in which the hydrocarbon—utilising microorganisms are selected from the genera consisting of Mycobacterium, Corynebacterium, Arthrobacter and Pseudomonas.

11. Process as claimed in claim 10 in which the hydrocarbon utilising microorganism is selected from the group consisting of *Mycobacterium rhodochrous* 7E1C NCIB 9703, *Mycobacterium lacticolum* NCIB 9739 and *Pseudomonas aeruginosa* 473.

12. Process as claimed in claim 7 in which the plastic carrier is polyethylene.

13. Process as claimed in claim 12 in which the hydrocarbon utilizing microorganism is selected from the group consisting of *Mycobacterium rhodochrous* 7E1C NCIB 9703, *C. hydrocarboxydans* ATCC 21761 and *Pseudomonas aeruginosa* 473.

* * * * *